United States Patent [19]
Vincent et al.

[11] Patent Number: 5,565,429
[45] Date of Patent: Oct. 15, 1996

[54] PEPTIDES DERIVED FROM TRIFLUOROMETHYLKETONES

[75] Inventors: Michel Vincent, Bagneux; Guillaume de Nanteuil, Suresnes; Georges Remond, Versailles; Bernard Portevin, Elancourt; Yolande Herve, Puteaux; Emmanuel Canet, Paris; Michel Lonchampt, Rungis, all of France

[73] Assignee: Adir et Compagnie, Courbevoie, France

[21] Appl. No.: 439,233

[22] Filed: May 11, 1995

Related U.S. Application Data

[63] Continuation of Ser. No. 99,915, Jul. 30, 1993, abandoned.

[30] Foreign Application Priority Data

Jul. 28, 1992 [FR] France ................... 92 09254

[51] Int. Cl.⁶ ............... A61K 38/00; C07K 5/00; C07K 7/00; C07K 17/00
[52] U.S. Cl. .............................. 514/18; 530/331
[58] Field of Search ............... 514/18; 530/331

[56] References Cited

U.S. PATENT DOCUMENTS 4,910,190  3/1990  Bergeson et al. ............. 514/19

OTHER PUBLICATIONS

Skiles et al., J. Med. Chem., vol. 35 pp. 641–662 (1992).
Trainor, Tips, vol. 8 pp. 303–307 (1987).
Watthney et al. J. Med. Chem. vol. 27 pp. 816–818 (1984).
TIPS vol. 8, 303–307 (1989).
American Review of Respiratory Disease vol. 133, 149–169 (1986).

*Primary Examiner*—Toni R. Scheiner
*Assistant Examiner*—Sheela J. Huff
*Attorney, Agent, or Firm*—The Firm of Gordon W. Hueschen

[57] ABSTRACT

Compounds of formula (I):

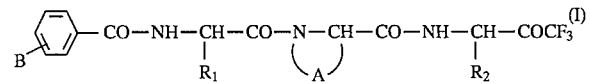

wherein:

$R_1$ represents an unsubstituted or substituted alkyl, $R_2$ represents an unsubstituted or substituted alkyl, A represents, with the nitrogen and carbon atoms to which it is attached, a nitrogenous mono- or polycyclic structure, and B represent any one of the radicals a through j as defined in the description, and medicaments containing the same, are useful as human leucocyte elastase inhibitors.

19 Claims, No Drawings

PEPTIDES DERIVED FROM TRIFLUOROMETHYLKETONES

The present application is a continuation of our prior-filed U.S. application Ser. No. 08/099,915, filed Jul. 30, 1993, and now abandoned.

The present invention relates to new peptides derived from trifluoromethyl ketones.

These new peptide compounds have inhibitory properties for human leucocyte elastase.

Elastin is an elastic fibrous protein of the connective tissue of vertebrates. It is present in vascular walls, skin, lungs, cartilages, ligaments and other tissues. Elastases are enzymes capable of solubilizing fibrous elastin. Human leucocyte elastase is a serine protease, which is found in the active form in azurophile granules of the polymorphonuclear neutrophile. It is a glycoprotein of 25 to 30 kDa formed from 218 amino acids. Human leucocyte elastase (HLE) solubilizes fibrous elastin but also cleaves other proteins of the extracellular matrix (collagens, fibronectin, proteoglycans, and the like) and hydrolyzes and inactivates a certain number of plasma proteins (clotting factor, immunoglobulin, complement, and the like). The elastolytic activity is controlled and regulated by natural inhibitors ($\alpha$-1-antitrypsin, $\alpha$-2-macroglobulin or bronchial inhibitor).

Reversible or irreversible inhibitors of human leucocyte elastase have been described in the literature for the treatment of physiopathologic situations where its role has been mentioned (D. A. Trainor, TIPS, 8, 303–307, 1987).

These pathological states can be pulmonary emphysema, rheumatoid arthritis, degenerative diseases of the connective tissue such as atherosclerosis (J. G. Bieth, "Elastases: Catalytic and Biological Properties" in "Regulation of matrix accumulation"—R. P. Mecham—Academic Press, N.Y., 217–320, 1986), acute respiratory distress syndrome in adults (P. M. Suter et al., Am. Rev. Respir. Dis., 145, 1016–1022, 1992), cystic fibrosis (K. C. Meyer et al., Am. Rev. Respir. Dis., 144, 580–585, 1991), chronic bronchitis (J. A. Nadel, Respiration, 58 (suppl. 1, 3–5), 1991), glomerulonephrites (E. Sanders et al., Renal. physiol., 3, 355–359, 1980), psoriasis (J. Schalkwijk et al., Br. J. Dermatology, 122, 631–644, 1990), tissue lesions arising during ischemia/reperfusion procedures (F. A. Nicolini et al., Am. Heart J., 122–1245, 1991 and C. R. B. Welbourn et al., Am. J. Physiol., 260, 1852–1856, 1991). It may also play a role in phenomena of normal or pathological/tumor invasion cell migration (J. G. Bieth cited above).

Recently, peptides derived from trifluoromethyl ketones have been described as HLE inhibitors. This is more particularly the case for the compounds described in Patents EP 189,305 and EP 369,391.

The present invention more specifically relates to the compounds of formula (I):

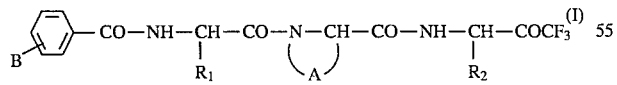

in which:

R$_1$ represents a linear or branched (C$_1$–C$_6$)alkyl radical which is unsubstituted or substituted by a (C$_3$–C$_7$)-cycloalkyl, phenyl, amino or benzyloxycarbonylamino, (3,5-di-tert-butyl- 4-hydroxy)benzylcarbonylamino, (3,5-di-tert-butyl-4-hydroxy)phenylthio or 3-[(3,5-di-tert-butyl-4-hydroxy)phenylthio]propylcarbonylamino radical, R$_2$ represents a linear or branched (C$_1$–C$_6$)alkyl radical which is unsubstituted or substituted by a (C$_3$–C$_7$)-cycloalkyl or phenyl radical, A represents, with the nitrogen and carbon atoms to which it is attached, a 2-azabicyclo[2.2.2]octane, 2-azabicyclo[2.2.1]heptane, perhydroindole, perhydroisoindole, indoline, isoindoline, perhydroquinoline, perhydroisoquinoline, 1,2,3,4-tetra-hydroquinoline, cyclopenta[b]pyrrolidine or 1,3-thiazolidine ring, represents any one of the following radicals:

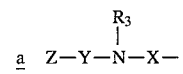

which:

R$_3$ represents a hydrogen atom or a linear or branched (C$_1$–C$_6$)alkyl radical which is unsubstituted or substituted by a phenyl radical, X, Y, which are different, represent CO or SO$_2$, Z represents
  a linear or branched (C$_1$–C$_6$)alkyl radical which is substituted by one or two, identical or different, (C$_3$–C$_7$)cycloalkyl or (C$_1$–C$_4$)trihaloalkyl radicals,
  an adamant-1-yl radical,
  a phenyl radical which is unsubstituted or-substituted by one or a number of, identical or different, halogen atoms or linear or branched (C$_1$–C$_6$)alkyl, hydroxyl, linear or branched (C$_1$–C$_6$)alkoxy, (C$_1$–C$_4$)trihaloalkyl, cyano, 1,4-dihydropyrid-4-yl (unsubstituted or substituted by one or a number of, identical or different, linear or branched (C$_1$–C$_6$)alkyl or linear or branched (C$_1$–C$_6$)-alkoxycarbonyl radicals), (3,5-di-tert-butyl- 4-hydroxy)benzylcarbonylaminosulfonyl, (3,5-di-tert-butyl-4-hydroxy)benzoyloxy, (3-ethoxy-2-hydroxy)propoxy or [3,5-di-tert-butyl-4-ethoxymethoxy)]benzyloxy radicals,
  or, a (C$_1$–C$_4$)alkenyl radical substituted by a [3,5-di-tert-butyl- 4-(ethoxymethoxy)]phenyl or (3,5-di-tert-butyl- 4-hydroxy)phenyl radical,

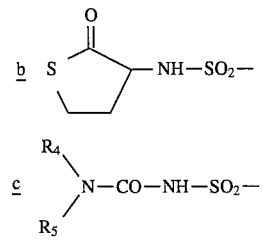

in which:

R$_4$, R$_5$, which are identical or different, represent: a hydrogen atom or a linear or branched (C$_1$–C$_6$)alkyl (unsubstituted or substituted by a phenyl group), phenyl (unsubstituted or substituted by one or a number of halogen atoms or linear or branched (C$_1$–C$_6$)alkyl, linear or branched (C$_1$–C$_6$)alkoxy or (C$_1$–C$_4$)trihaloalkyl radical), 3-azabicyclo[3.3.0]oct-3-yl, 4-(2,3,4-tri-methoxybenzyl)piperazino, morpholino, pyrrolidino, piperidino, azetidino or 1-oxa-3, 8-diaza-2-oxospiro[4.5]dec-8-yl (unsubstituted or substituted by a linear or branched (C$_1$–C$_6$)alkyl or linear or branched (C$_1$–C$_6$)phenylalkyl radical) radical, or form, with the nitrogen atom to which they are attached, any one of the following rings:
  3-azabicyclo [3.3.0]octane,
  4-(2,3,4-trimethoxybenzyl)piperazine, morpholine,
pyrrolidine,
azetidine,
3,8-diaza-1-oxa-2-oxospiro[4.5]decane which is unsubstituted or substituted by a linear or branched $(C_1-C_6)$alkyl or linear or branched $(C_1-C_6)$phenylalkyl radical, d) [structure: benzene ring with $R_6$ substituent, bearing a $-CO-CH(-)-$ ketone group and an $-SO_2-N(R_3)-$ group forming a ring]

in which:
$R_3$ is as defined above and
$R_6$ represents a hydrogen or halogen atom or a linear or branched $(C_1-C_6)$alkyl, linear or branched $(C_1-C_6)$alkoxy, $(C_1-C_4)$trihaloalkyl or cyano radical, e) [structure: spirocyclic oxazolidinone-piperidine with $N-R_3$ and $N-T$]

in which:
$R_3$ is as defined above,
T represents any one of the following groups:
  $-(CH_2)m-$,
  $-SO_2-NH-CO-$,
  $-CO-NH-SO_2-$, $-(CH_2)_m-$[phenyl]$-SO_2-NH-CO-$, $-(CH_2)_m-$[phenyl]$-CO-NH-SO_2-$, such that m is an integer between 1 and 4, f₁) $R_7-(CH_2)_n-$[phenyl]$_{n'}-CO-NH-X-$ f₂) $R_7-(CH_2)_n-$ in which:
X is as defined above,
n is equal to 0, 1, 2 or 3,
n' is equal to 0 or 1,
$R_7$ represents a:
  3,5-di-tert-butyl-4-hydroxyphenyl,
  3,5-di-tert-butyl-4-hydroxyphenoxy,
  or 3,5-di-tert-butyl-4-hydroxyphenylthio radical g) [structure: 3,5-di-tert-butyl-4-hydroxyphenyl with $-C(CH_3)_2-(CH_2)_p-CO-NH-SO_2-$]

in which p is equal to 1 or 2, h) [structure: benzene with ortho $-CO-NH-SO_2-$ and $-CO-N$ of thiazolidine ring]

i) $R_3-S-CH_2-CH(NH-CO-CH_3)-CO-NH-SO_2-$ in which $R_3$ is as defined above, j) $-SO_2-NH-CO-CH(NH-CO-CH_3)-CH_2-S-S-CH_2-$

[structure: $CF_3-CO-CH(CH(CH_3)_2)-NH-CO-CH(-N\underset{A}{\frown}-)-CO-CH(CH(CH_3)_2)-NH-CO-$[phenyl]$-CH(NH-CO-CH_3)-CO-NH-SO_2-$]

in which A is as defined above, which compounds of formula (I) comprise the corresponding hydrates of the $COCF_3$ ketone functional group, their enantiomers, diastereoisomers and epimers and their addition salts with a pharmaceutically acceptable acid or base.

Among the pharmaceutically acceptable acids, there may be mentioned, as non-limiting, hydrochloric, sulfuric, tartaric, maleic, fumaric, methanesulfonic or camphoric acids, and the like.

Among the pharmaceutically acceptable bases, there may be mentioned, as non-limiting, sodium hydroxide, potassium hydroxide, tert-butylamine, diethylamine, ethylenediamine, and the like.

The invention also applies to the process for the preparation of the compounds of formula (I), characterized in that there is used, as starting material, an alcohol of formula (II), the isomers of which have optionally been separated by a conventional separation technique:

$$H_2N-CH(R_2)-CH(OH)(CF_3) \quad (II)$$

in which $R_2$ has the same meaning as in formula (I), which is reacted:

a either with a protected amino acid of formula (III), the isomers of which have optionally been separated according to a conventional separation technique, by a conventional peptide coupling technique such as that described by W. Konig and R. Geiger (Ber., 103, 788, 1970):

$$Boc-N\underset{A}{\frown}-CH-CO_2H \quad (III)$$

in which A has the same meaning as in formula (I) and Boc represents a tert-butoxycarbonyl group, to lead to the compound of formula (IV):

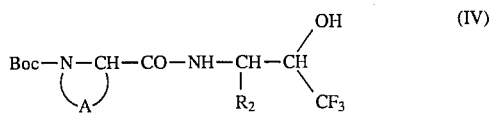

in which A, R$_2$ and Boc have the same meaning as above, which compound of formula (IV) is:
* either deprotected by acid hydrolysis to lead to the compound of formula (V):

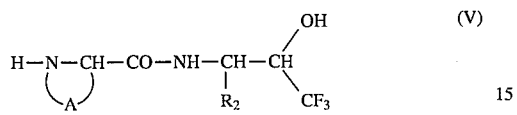

in which A and R$_2$ have the same meaning as above, which is reacted with a protected amino acid of formula (VI), the isomers of which have optionally been separated according to a conventional separation technique, in the presence of a conventional coupling agent for peptide synthesis:

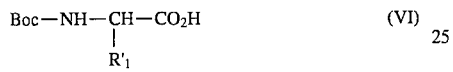

in which Boc represents a butoxycarbonyl radical and R'$_1$ represents a linear or branched (C$_1$-C$_6$)alkyl radical which is unsubstituted or substituted by a (C$_3$C$_7$)cycloalkyl, phenyl or benzyloxycarbonylamino radical, to lead to the compound of formula (VII):

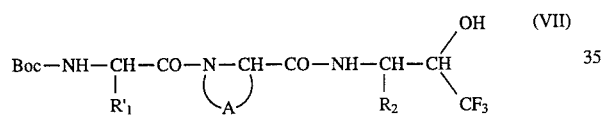

in which Boc, R'$_1$, A and R$_2$ have the same meaning as above, which is oxidized to lead to the compound of formula (VIII), the isomers of which are optionally separated according to a conventional separation technique,

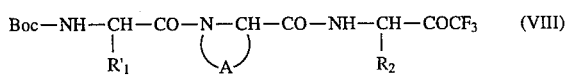

in which Boc, R'$_1$, A and R$_2$ have the same meaning as above,

* or is oxidized to lead to the compound of formula (X):

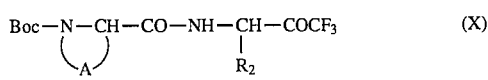

in which Boc, A, and R$_2$ have the same meaning as above, which is deprotected in acid medium to lead to the compound of formula (XI):

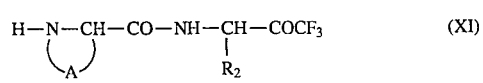

in which A and R$_2$ have the same meaning as above, which is reacted with a protected amino acid of formula (VI) as defined above, to lead to the compound of formula (VIII) defined above, b or with a protected dipeptide of formula (XII), obtained by conventional coupling of two amino acids in the racemic form or in the form of pure enantiomers,

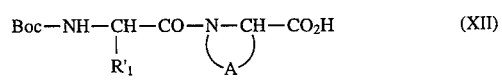

in which Boc, R'$_1$ and A have the same meaning as above, to lead to the compound of formula (VII) defined above, which is oxidized and leads to the compound of formula (VIII) defined above, which compound of formula (VIII) is deprotected in acid medium, to lead to the compound of formula (IX), the isomers of which are optionally separated according to a conventional separation technique,

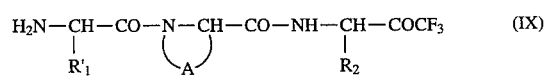

in which R'$_1$, A and R$_2$ have the same meaning as above, which is reacted with an acid of formula (XIII), according to a conventional peptide coupling technique,

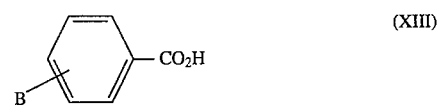

in which B has the same meaning as in formula (I), to lead to the compound of formula (I/a), a specific case of the compounds of formula (I),

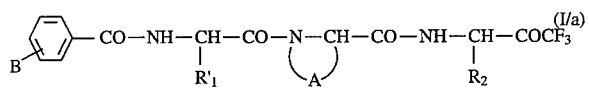

in which B, A, R'$_1$ and R$_2$ have the same meaning as above, which, when R'$_1$ represents an alkyl radical substituted by a benzyloxycarbonylamino group, is deprotected, if desired, by catalytic hydrogenation, to lead to the compound of formula (I/b), a specific case of the compounds of formula (I),

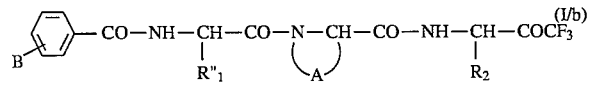

in which B, A and R$_2$ have the same meaning as in formula (I) and R"$_1$ represents an alkyl substituted by an amino radical, which compounds of formula (I/a) and (I/b) are purified according to a conventional purification technique, the isomers of which are separated, if desired, according to a conventional separation technique, and then, if necessary, are converted to an addition salt with a pharmaceutically acceptable acid or base.

The compounds of formula (I) have very advantageous pharmacological properties, in particular properties inhibitory for human leucocyte elastase. As such, they can be used with advantage in a certain number of therapeutic indications such as pulmonary emphysema, chronic bronchitis, acute respiratory distress syndrome in adults, cystic fibrosis, rheumatoid arthritis, glomerulonephritis, inflammations, ischemia reperfusion syndromes, phenomena of invasion and diffusion of malignant cells, degenerative diseases of connective tissue or skin aging.

The inhibitory activity for human leucocyte elastase was demonstrated by in vitro and in vivo tests. The compounds showed greater inhibitory activities than the reference materials, such as chloromethyl ketone or dichloroisocoumarin.

The substituents of the compounds of formula (I) have made it possible to add, to the inhibitory activity for human leucocyte elastase, properties of antiinflammatory, antiradical and/or mucoregulatory type.

Another subject of the present invention is the pharmaceutical compositions containing, as active principle, at least one compound of general formula (I) or one of its addition salts with a pharmacologically acceptable acid or base, alone or in combination with one or a number of nontoxic, inert excipients or vehicles.

Among the pharmaceutical compositions according to the invention, there can more particularly be mentioned those which are suitable for oral, parenteral or nasal administration, simple or sugar-coated tablets, sublingual tablets, gelatin capsules, troches, suppositories, creams, ointments, dermal gels, aerosols, drinkable and injectable phials, and the like.

The useful dose varies depending on the age and weight of the patient, the nature and severity of the ailment and on the administration route.

The latter can be oral, nasal, rectal or parenteral. Generally, the unit dose ranges between 10 μg and 300 mg for a treatment taken 1 or 3 times per 24 hours.

A preferential administration route for the derivatives of the invention is the aerosol route, in the form of a powder or of a liquid aerosol.

The following examples illustrate the invention and do not limit it in any way.

The starting materials used are known products or products prepared according to known procedures. The abbreviations used in the examples are the following:

Abo in place of 2-azabicyclo[2.2.2]octane-3-carbonyl
Boc in place of tert-butoxycarbonyl
Val in place of valyl
Phi in place of perhydroindole-2-carbonyl
Abh in place of 2-azabicyclo[2.2.1]heptane-3-carbonyl
Lys in place of lysyl
Cys in place of cysteinyl Preparations A to V describe starting materials which are useful in the synthesis of the compounds of formula (I).

Preparation A: 4-(4-Chlorobenzoylaminosulfonyl)benzoic acid 60 mmol of 4-carbethoxybenzenesulfonamide and a solution containing 60 mmol of 4-dimethylaminopyridine in 40 ml of dimethylformamide (DMF) are added successively to a solution containing 60 mmol of parachlorobenzoic acid in 100 ml of DMF. The whole is maintained at room temperature with stirring for 20 hours, filtered and then evaporated. The oil obtained is purified by chromatography on a silica column, using a dichloromethane/ethanol (93/7) mixture as solvent, and leads to ethyl 4-(4-chlorobenzoylaminosulfonyl)benzoate which is saponified by stirring for 20 hours in a mixture containing 48 ml of 1N sodium hydroxide solution and 60 ml of ethanol. After evaporation, addition of 100 ml of water and then 50 ml of 1N hydrochloric acid, the expected product precipitates and is filtered and washed with water and dichloromethane.

Melting point: 265° C.

Preparation B: 4-[(2-Oxotetrahydrothiophen-3-yl)aminosulfonyl]benzoic acid 50 mmol of homocysteinethiolactone hydrochloride and 100 mmol of triethylamine in 30 ml of dioxane are added simultaneously at room temperature to 50 mmol of 4-chlorosulfonylbenzoic acid in 120 ml of dioxane. Stirring is maintained for 18 hours and the solvent evaporated. The residue is taken up in water and extracted with ethyl acetate. After drying and evaporation, the expected product is obtained after purification on a silica column, using a dichloromethane/ethyl acetate (90/10) mixture as eluent.

Melting point: 146° C.

Preparation C: 4-[2-(1-Oxa-2-oxo-3,8-diazaspiro[4.5]dec-8-yl)ethyl]benzoic acid 100 mmol of 4-(2-chloroethyl)benzoic acid and 100 mmol of 1-oxa- 2-oxo-3,8-diazaspiro[4.5]decane are dissolved in 300 ml of methyl isobutyl ketone in the presence of 300 mmol of potassium carbonate and 0.25 g of potassium iodide. The whole is maintained for 30 hours at reflux, with stirring, and then evaporated. The residue is taken up in water and washed with ethyl acetate. The aqueous phase is acidified with concentrated hydrochloric acid (pH=1), filtered and the expected product is fixed to resin, washed with water and eluted with 20% aqueous ammonia. After evaporation, the expected product is obtained after purification on a silica column, using an acetone/water (90/10) mixture as eluent.

Melting point:>250° C.

Preparation D: 4-[2-(4-Hydroxy-3,5-di-tert-butylphenylthio)ethyl]benzoic acid 50 mmol of 4-hydroxy-3,5-di-tert-butylthiophenol, 50 mmol of 4-(2-chloroethyl)benzoic acid and 100 ml of dimethylformamide are added, with stirring and under an inert atmosphere, to a solution containing 50 mmol of sodium ethoxide in 200 ml of ethanol. The whole is heated at 65°–70° C. for 8 hours. The ethanol is evaporated, the remaining phase taken up in ethyl acetate, filtered and evaporated. The expected product is obtained by purification of the residue by chromatography on silica gel, using a dichloromethane/dioxane (95/5) mixture as eluent.

Melting point: 147° C.

Elemental microanalysis:

|  | C % | H % | S % |
|---|---|---|---|
| calculated | 71.47 | 7.82 | 8.29 |
| found | 71.01 | 8.04 | 8.02 |

Preparation E: 4-[4-[2-(4-Hydroxy-3,5-di-tert-butylphenylthio)ethyl]benzoylaminosulfonyl]benzoic acid 6 mmol of N-methylmorpholine are added to 6 mmol of the compound obtained in Preparation D in 70 ml of anhydrous tetrahydrofuran (THF) under an inert atmosphere and the whole is cooled to 5° C. 6 mmol of isobutyl chloroformate in a solution of 10 ml of anhydrous THF are then slowly added. After returning to room temperature, the whole is stirred for 30 minutes. 6 mmol of 4-carbethoxyphenylsulfonamide in 25 ml of anhydrous THF are then slowly added and stirring is maintained for 18 hours. After evaporation, the residue is taken up in ethyl acetate, washed with a saturated sodium bicarbonate solution, with 10% citric acid and with water, dried and evaporated. The ester thus obtained is purified by chromatography on a silica column, using a dichloromethane/methanol/aqueous ammonia (90/10/1) mixture as the elution solvent. The expected product is then obtained by saponification of the ester.

Preparation F: 4-[(2,5,7,8-Tetramethyl-6-hydroxychroman-2-yl)carbonylaminosulfonyl]benzoic acid The expected product is obtained by using the same process as that described in Preparation A.

Melting point: 128° C.

Preparation G: 4-[S-tert-Butyl-N-acetylcysteinylaminosulfonyl]benzoic acid

The expected product is obtained by using the same process as that described in Preparation A.

Melting point: 227° C.

Preparation H: 4-[2-[(1,3-Thiazolidin-3-yl)carbonyl]benzoylaminosulfonyl]benzoic acid The expected product is obtained by using the same process as that described in Preparation A.

Melting Doint:>250° C.

Preparation I: 4-[(4-Hydroxy-2-methyl-1,1-dioxo-1,2-benzothiazin- 3-yl)carbonyl]benzoic acid Stage A: N-[(4-Carbethoxybenzoyl)methyl]saccharin 45 mmol of ethyl 4-bromoacetylbenzoate in 120 ml of dimethylformamide and 48 mmol of sodium saccharinate are maintained at 100° C. for 180 minutes. After evaporation of the solvent, taking up in 200 ml of water, extraction with dichloromethane, drying and evaporation, the residue is taken up in isopropyl ether, then filtered and taken to the expected product.

Stage B: 3-(4-Carbethoxybenzoyl)-1,1-dioxo-1,2-benzothiazin- 4-one

The expected product is obtained from the compound described in Stage A according to the method described by H. Zinner et al. (J. O. C., 30, 2241–2246, 1965).

Melting point: 161° C.

Stage C: 3-(4-Carbethoxybenzoyl)-2-methyl-1,1-dioxo-1, 2-benzothiazin- 4-one

The expected product is obtained from the compound described in Stage B according to the method described by H. Zinner et al. (J. O. C., 30, 2241–2246, 1965).

Stage D: 4-[(4-Hydroxy-2-methyl-1,1-dioxo-1,2-benzothiazine- 3-yl)carbonyl]benzoic acid The expected product is obtained by saponification of 7 mmol of the compound obtained in the preceding stage in 30 ml of 0.5N sodium hydroxide solution and 15 ml of ethanol for 48 hours. After evaporation of the ethanol and acidification with 20 ml of 1N hydrochloric acid, the precipitate is filtered and washed with water.

Melting point:>260° C.

Preparation J: 4-[(Dicyclopropylmethyl)carbonylaminosulfonyl]benzoic acid

The expected product is obtained by using the same process as that described in Preparation A, using dicyclohexylcarbodiimide as the coupling agent.

Elemental microanalysis:

|  | C % | H % | N % | S % |
|---|---|---|---|---|
| calculated | 55.72 | 5.30 | 4.33 | 9.92 |
| found | 55.93 | 5.38 | 4.89 | 9.99 |

Preparation K: 4-[(4-Chlorophenyl)ureidosulfonyl]benzoic acid

The compound was obtained according to the technique described in Synthesis, 3, 221, 1990.

Elemental microanalysis:

|  | C % | H % | N % | S % |
|---|---|---|---|---|
| calculated | 50.20 | 3.95 | 7.32 | 8.38 |
| found | 50.30 | 3.96 | 7.53 | 8.15 |

Preparation L: 4-[(Adamant-1-yl)carbonylaminosulfonyl] benzoic acid 25 mmol of the chloride of adamantane-1-carboxylic acid and 25 mmol of 4-ethoxycarbonylbenzene- sulfonamide are maintained at reflux of 100 ml of anhydrous toluene in the presence of 3.45 ml of triethylamine for 20 hours. After cooling, the toluene phase is washed with water, then with a NaHCO₃ solution and then again with water. The ester thus obtained is purified by chromatography on a silica column, using a dichloromethane/acetone (98/2) mixture as eluent. The expected product is then obtained by saponification of the ester in a sodium hydroxide/ethanol mixture and is purified by chromatography on a silica column, using a dichloromethane/methanol (90/10) mixture as eluent.

Preparation M: 4-[(3,5-Di-tert-butyl-4-hydroxybenzyl)carbonylaminosulfonyl]benzoic acid The expected product was prepared according to the process described in Preparation J.

Elemental microanalysis:

|  | C % | H % | N % | S % |
|---|---|---|---|---|
| calculated | 61.73 | 6.53 | 3.13 | 7.16 |
| found | 61.37 | 6.60 | 3.35 | 7.07 |

Preparation N: 4-[4-(2,6-Dimethyl-3,5-diethoxycarbonylpyrid-4-yl)benzoylaminosulfonyl]benzoic acid The expected product was prepared according to the process described in Preparation J, using 1-(3-dimethylaminopropyl)-3ethylcarbodiimide as the coupling agent.

Preparation O: 4-{4-[2-(1-Oxa-2-oxo-3,8-diazaspiro[4.5]-dec-8 -yl)ethyl]benzoylaminosulfonyl}-benzoic acid The expected product was prepared according to the process described in Preparation N from the compound described in Preparation C and 4-ethoxycarbonylbenzenesulfonamide.

Preparation P: 4-{4-Chloro-3-[(3,5-di-tert-butyl-4-hydroxybenzyl)carbonylaminosulfonyl] benzoylaminosulfonyl}benzoic acid The expected product was obtained by coupling 4-hydroxy-3,5-di-tert-butylphenylacetic acid with ethyl 4-chloro-3-sulfamoylbenzoate according to the process described in Preparation J, saponification and then again coupling the compound obtained with 4-ethoxycarbonylbenzenesulfonamide.

Preparation Q: 4-[3,5-Di-tert-butyl-4-(3,5-di-tert- butyl-4 -hydroxybenzoyloxy)benzoylaminosulfonyl]benzoic acid The expected product was obtained according to the process described in Preparation J.

Elemental microanalysis:

|  | C % | H % | N % | S % |
|---|---|---|---|---|
| calculated | 66.74 | 7.11 | 2.10 | 4.82 |
| found | 66.38 | 7.48 | 2.23 | 5.20 |

Preparation R: 4-{[4-Methoxy-3-(3-ethoxy-2-hydroxypropoxy)benzoyl]aminosulfonyl}benzoic acid The expected product was prepared from 4-methoxy-3-(2,3-epoxypropoxy)benzoic acid and 4-ethoxycarbonylbenzenesulfonamide according to the process described in Preparation N.

Mass spectrum: Chemical ionization/NH₃ [M+H]⁺: m/z= 454 (theoretical mass M=453 )

Preparation S: 4-[(3,5-Di-tert-butyl-4-hydroxy)benzoylaminosulfonyl]benzoic acid The compound was obtained according to the process described in Preparation J.

Preparation T: 4-{4-[3,5-Di-tert-butyl-4-(ethoxymethoxy)benzyloxy]benzoylaminosulfonyl}benzoic acid The compound was prepared according to the process described in Preparation J.

Preparation U: 4-[(3,5-Di-tert-butyl-4-hydroxyphenylthio)acetylaminosulfonyl]benzoic acid The compound was prepared according to the process described in Preparation J.

Preparation V: 4-{[3-(3,5-Di-tert-butyl-4-ethoxymethoxyphenyl)-trans-acryloyl]aminosulfonyl}benzoic acid The compound was prepared according to the process described in Preparation J.

Elemental microanalysis:

|            | C %   | H %  | N %  | S %  |
|------------|-------|------|------|------|
| calculated | 62.65 | 6.82 | 2.71 | 6.19 |
| found      | 62.46 | 7.25 | 2.93 | 6.56 |

EXAMPLE 1

4-(4-Chlorobenzoylaminosulfonyl)benzoyl-(S)-Val-(S)-Abo-(R,S)-Val-CF$_3$

Stage A: Boc-(S)-Val-(S)-Abo-OCH$_2$CH$_3$

By using the peptide coupling technique described by W. Konig and R. Geiger (Chem. Ber., 103, 788, 1970), 100 mmol of Boc-(S)-Val-OH and 100 mmol of 3-(S)-carbethoxy-2-azabicyclo[2.2.2]octane are reacted. The expected product then obtained after purification on silica gel, using a dichloromethane/ethanol (97/3) mixture as eluent.

Yield: 80%

Elemental microanalysis:

|            | C %   | H %  | N %  |
|------------|-------|------|------|
| calculated | 62.80 | 8.96 | 7.32 |
| found      | 62.42 | 8.78 | 7.26 |

Stage B: Boc-(S)-Val-(S)-Abo-OH

The expected product is obtained by saponification of the compound obtained in the preceding stage in a solution containing 150 ml of ethanol and 100 ml of 1N sodium hydroxide solution for 72 hours. After evaporation of the ethanol and addition of 200 ml of water, washing the aqueous phase with ether and acidification of this by addition of citric acid, the compound precipitates and is washed with water and then with ether.

Yield: 80%

Melting point: 186° C.

Stage C: N-(Boc-(S)-Val-(S)-Abo)-1-isopropyl-2-hydroxy-3,3,3-trifluoropropylamine 21 mmol of the compound obtained in the preceding stage and 21 mmol of 1-isopropyl-2-hydroxy-3,3,3-trifluoropropylamine hydrochloride (described in J. Med. Chem., 33., 394–407, 1990) are coupled according to the peptide coupling technique described in Stage A. The expected product is obtained after purification on silica gel, using a dichloromethane/ethanol (97.5/2.5) mixture as eluent.

Yield: 96%

15 Elemental microanalysis:

|            | C %   | H %  | N %  |
|------------|-------|------|------|
| calculated | 56.79 | 7.94 | 8.28 |
| found      | 56.65 | 7.74 | 8.48 |

Stage D: Boc-(S)-Val-(S)-Abo-(R,S)-Val-CF$_3$ 5 mmol of the compound obtained in the preceding stage are dissolved in 30 ml of dimethyl sulfoxide and 30 ml of acetic anhydride. After stirring for 20 hours at room temperature and addition of 75 ml of water, stirring is maintained for an additional hour. The whole is poured onto 150 ml of water and basified by addition of sodium bicarbonate. After extraction with dichloromethane, washing the organic phases with water, drying and evaporation, the expected product is obtained after purification on a silica column, using a dichloromethane/acetone (90/10 ) mixture as eluent.

Yield: 65%

Elemental microanalysis:

|            | C %   | H %  | N %  |
|------------|-------|------|------|
| calculated | 57.02 | 7.58 | 8.31 |
| found      | 57.69 | 7.58 | 8.12 |

Stage E: (S)-Val-(S)-Abo-(R,S)-Val-CF$_3$ hydrochloride 7 mmol of the product obtained in the preceding stage are deprotected by stirring, at room temperature, in 100 ml of a 3N hydrochloric acid solution in ethyl acetate. After evaporation of the solvent and addition of 100 ml of ether, the gel thus obtained is dried and taken to the expected product.

Yield: 90%

Stage F: 4-(4-Chlorobenzoylaminosulfonyl)benzoyl-(S)-Val-(S)-(R,S)-Val-CF$_3$ 1 mmol of the product obtained in the preceding stage and 1 mmol of 4-(4-chlorobenzoylaminosulfonyl)-benzoic acid described in Preparation A are coupled according to the technique described by B. Castro et al. (Tet. Lett., 14, 1219–1222, 1975). After evaporation of the dimethylformamide, the residue is dissolved in 100 ml of ethyl acetate, washed with 50 ml of a saturated sodium bicarbonate solution and then with water. After drying and evaporation, the expected product is obtained by chromatography on silica gel, using a dichloromethane/methanol (90/10) mixture as eluent.

Yield: 60%

Mass spectrum: FAB–[M+H]$^+$: m/z=727 (theoretical mass–$^{35}$Cl–M=726)

Examples 2 to 20 have been obtained by using the same process as that described for Example 1, using the corresponding starting materials.

EXAMPLE 2

4-{[3-(3-Azabicyclo[3.3.0]octane)ureido]sulpfonyl}benzoyl-(S)-Val-(S)-Abo-(R,S)-Val-CF$_3$ Mass spectrum: FAB–[M+H]$^+$: m/z=741 (theoretical mass M=740)

EXAMPLE 3

4-(4-Chlorophenylsulfonylaminocarbonyl)benzoyl-(S)-Val-(S)-Abo-(R,S)-Val-CF$_3$

Mass spectrum: FAB–[M–H]$^-$: m/z=725 (theoretical mass–$^{35}$Cl–M=726)

EXAMPLE 4

4-(4-Chlorophenylsulfonylaminocarbonyl)benzoyl-(S)-Val-(S)-Abo-Val-CF$_3$, α isomer Mass spectrum: FAB–[M–H]$^-$: m/z=725 (theoretical mass–$^{35}$Cl–M=726)

EXAMPLE 5

4-(4-Chlorophenylsulfonylaminocarbonyl)benzoyl-(S)-Val-(S)-Abo-Val-CF$_3$, β isomer Mass spectrum: FAB–[M–H]$^-$: m/z=725 (theoretical mass–$^{35}$Cl–M=726)

The α and β isomers of the compound of Example 3 are separated by C$_{18}$ reverse phase preparative liquid chromatography, using a 0.05M NaHCO$_3$-water/acetonitrile (80/20) mixture as eluent. The eluates are concentrated, acidified with 10% citric acid, extracted with dichloromethane, washed with water, dried and evaporated. The α and β isomers are named thus by the order of departure from the column.

EXAMPLE 6

4-(4-Chlorophenylsulfonylaminocarbonyl)benzoyl-(S)-Val-( 2S,3aS,7aS)-Phi-(R,S)-Val-CF$_3$ Mass spectrum: FAB–[M–H]$^-$: m/z=739 (theoretical mass–$^{35}$Cl–M=740)

EXAMPLE 7

4-(4-Chlorophenylsulfonylaminocarbonyl)benzoyl-(S)-Val-( 2S,3aS,7aS)-Phi-Val-CF$_3$, α isomer Mass spectrum: FAB–[M–H]$^-$: m/z=739 (theoretical mass–$^{35}$Cl–M=740)

EXAMPLE 8

4-(4-Chlorophenylsulfonylaminocarbonyl)benzoyl-(S)-Val-( 2S,3aS,7aS)-Phi-Val-CF$_3$, β isomer Mass spectrum: FAB–[M–H]$^-$: m/z=739 (theoretical mass–$^{35}$Cl–M=740)

The α and β isomers of the compound of Example 6 are separated according to the same technique as that described for Examples and 5. The elution solvent is a mixture: 0.05M NaHCO$_3$-water/acetonitrile: 75/25.

EXAMPLE 9

4-[(R,S)-2-Oxotetrahydrothiophen-3-yl)aminosulfonyl]-benzoyl-(S)-Val-(S)-Abo-(R,S)-Val-CF$_3$ Mass spectrum: FAB–[M–H]$^-$: m/z=687 (theoretical mass–M=688)

EXAMPLE 10

4-[(2-Oxotetrahydrothiophen-3-yl)aminosulfonyl]benzoyl-(S)-Val-(S)-Abo-Val-CF$_3$, mixture of α isomers Mass spectrum: FAB–[M–H]$^-$: m/z=687 (theoretical mass–M=688)

EXAMPLE 11

4-[(2-Oxotetrahydrothiophen-3-yl)aminosulfonyl]benzoyl-(S)-Val-(S)-Abo-Val-CF$_3$, mixture of β isomers Mass spectrum: FAB–[M–H]$^-$: m/z=687 (theoretical mass–M=688)

The expected products are obtained by using the product described in Preparation B in Stage F. The compound of Example is a mixture of 4 isomers, two pairs of which are separated according to the technique described for Examples 4 and 5. The elution solvent is a mixture: 0.05M NaHCO$_3$-water/acetonitrile: 65/35.

EXAMPLE 12

4-[2-(1-Oxa-2-oxo-3,8-diazaspiro[4.5]dec-8-yl)ethyl]benzoyl-(S)-Val-(S)-Abo-(R,S)-Val- CF$_3$ The expected product is obtained by using the product described in Preparation C in Stage F.

Mass spectrum: FAB–[M+H]$^+$: m/z=692 (theoretical mass–M=691)

EXAMPLE 13

4-[4-[2-(1-Oxa-2-oxo-3,8-diazaspiro[4.5]dec-8-yl)ethyl]benzoylaminosulfonyl]benzoyl-(S)-Val-(S)-Abo-(R,S)-Val-CF$_3$

EXAMPLE 14

4-[(4-Hydroxy-3,5-di-tert-butylphenylacetyl)aminosulfonyl]benzoyl-(S)-Val-(S)-Abo-(R,S)-Val-CF$_3$ Elemental microanalysi:

|  | C % | H % | N % | S % |
| --- | --- | --- | --- | --- |
| calculated | 60.42 | 6.88 | 6.71 | 3.84 |
| found | 60.96 | 7.20 | 7.25 | 3.38 |

EXAMPLE 15

4-[2-(4-Hydroxy-3,5-di-tert-butylphenylthio)ethyl]benzoyl-(S)-Val-(S)-Abo-(R,S)-Val-CF$_3$ The expected product is obtained by using the product described in Preparation D in Stage F.

Elemental microanalysis:

|  | C % | H % | N % | S % |
| --- | --- | --- | --- | --- |
| calculated | 65.18 | 7.55 | 5.43 | 4.14 |
| found | 65.28 | 7.77 | 5.23 | 4.03 |

EXAMPLE 16

4-[4-[2-(4-Hydroxy-3,5-di-tert-butylphenylthio)ethyl]benzoylaminosulfonyl]benzoyl-(S)-Val-(S)-Abo-(R,S)-Val-CF$_3$ The expected product is obtained by using the product described in Preparation E in Stage F.

EXAMPLE 17

4-[(2,5,7,8-Tetramethyl-6-hydroxychroman-2-yl)carbonylaminosulfonyl]benzoyl-(S)-Val-(S)-Abo-(R,S)-Val-CF$_3$ The expected product is obtained by using the product described in Preparation F in Stage F.

Elemental microanalysis:

|  | C % | H % | N % | S % |
|---|---|---|---|---|
| calculated | 58.52 | 6.26 | 6.82 | 3.91 |
| found | 58.50 | 6.51 | 7.04 | 3.65 |

EXAMPLE 18

4-[S-tert-Butyl-N-acetyl-(S)-cysteinylaminosulfonyl]benzoyl-(S)-Val-(S)-Abo-(R,S)-Val- CF$_3$ The expected product is obtained by using the product described in Preparation G in Stage F.

Elemental microanalysis:

|  | C % | H % | N % | S % |
|---|---|---|---|---|
| calculated | 53.22 | 6.38 | 8.87 | 8.12 |
| found | 53.22 | 6.28 | 8.57 | 8.38 |

EXAMPLE 19

4-[2-[(1,3-Thiazolidin-3-yl)carbonyl]benzoylaminosulfonyl]benzoyl-(S)-Val-(S)-Abo-(R,S)-Val-CF$_3$ The expected product is obtained by using the product described in Preparation H in Stage F.

EXAMPLE 20

4-[(4-Hydroxy-2-methyl-1,1-dioxo-1,2-benzothiazin-3-yl)carbonyl]benzoyl-(S)-Val-(S)-Abo-(R,S)-Val-CF$_3$ The expected product is obtained by using the product described in Preparation I in Stage F.

Elemental microanalysis:

|  | C % | H % | N % | S % |
|---|---|---|---|---|
| calculated | 57.90 | 5.53 | 7.50 | 4.29 |
| found | 57.53 | 5.53 | 7.48 | 4.30 |

EXAMPLE 21

4-[(4-Hydroxy-1,1-dioxo-(2H)-1,2-benzothiazin-3-yl)carbonyl]benzoyl-(S)-Val-(S)-Abo-(R,S)-Val-CF$_3$ The expected product is obtained by using, in Stage F, the product synthesized by saponification of the compound described in Preparation I.

Mass spectrum: FAB–[M+H]$^+$: m/z=733 (theoretical mass–M=732)

EXAMPLE 22

4-(4-Chlorophenylsulfonylaminocarbonyl)benzoyl-(S)-Val-(1S,3S,4R)-Abh-(R,S)-Val-CF$_3$ Stage A: N-[(1S,3S,4R)-Abh]-2-hydroxy-1-isopropyl-3,3,3-trifluoropropylamine hydrochloride 21 mmol of Boc-(1S,3S,4R)-Abh-OH are coupled, according to the peptide coupling technique of W. Konig and R. Geiger, with 21 mmol of 2-hydroxy-1-isopropyl-3,3,3-trifluoropropylamine hydrochloride. The expected product is obtained after purification on a silica column, using a dichloromethane/methanol (97/3) mixture as eluent.

Stage B: N-[Boc-(S)-Val-(1S,3S,4R)-Abh]-2-hydroxy-1-isopropyl- 3,3,3-trifluoropropylamine The expected product is obtained by coupling 12 mmol of the compound described in Stage A with 12 mmol of Boc-(S)-Val-OH according to the same peptide coupling technique, and is purified by chromatography on a silica column, using a dichloromethane/ethanol (95/5) mixture as elution solvent.

Stage C: Boc-(S)-Val-(1S,3S,4R)-Abh-(R,S)-Val-CF$_3$

The expected product is obtained by oxidation of the compound described in Stage B, according to the same process as that described in Stage D of Example 1, and is purified by chromatography on a silica column, using a dichloromethane/acetone (93/7) mixture as eluent.

Stage D: (S)-Val-(1S,3S,4R)-Abh-(R,S)-Val-CF$_3$ hydrochloride

The expected product is obtained by deprotecting the compound described in Stage C according to the same technique as that described in Stage E of Example 1.

Stage E: 4-(4-Chlorophenylsulfonylaminocarbonyl)benzoyl-(S)-Val-(1S,3S,4R)-Abh-(R,S)-Val-CF$_3$ The expected product is obtained according to the process described in Stage F of Example 1 by reacting the compound described in Stage D with 4-(4-chlorophenylsulfonylaminocarbonyl)benzoic acid and is purified by chromatography on a silica column, using a dichloromethane/methanol (90/10) mixture and eluent.

Mass spectrum: FAB–[M+H]$^+$: m/z=713 (theoretical mass–$^{35}$Cl–M=712)

EXAMPLE 23

4-[2-[(1,3-Thiazolidin-3-yl)carbonyl]benzoylaminosulfonyl]benzoyl-(S)-Val-(1S,3S,4R)-Abh-(R,S)-Val-CF$_3$ The expected product is obtained according to the process described in Example 22 by using the product described in Preparation H in Stage E.

Mass spectrum: FAB–[M+H]$^+$: m/z=794 (theoretical mass–M=793)

Examples 24 to 39 were obtained according to the same process as that described in Example 1, using the corresponding starting materials.

EXAMPLE 24

4-[(Dicyclopropylmethyl)carbonylaminosulfonyl]benzoyl-(S)-Val-(S)-Abo-(R,S)-Val-CF$_3$ The expected product is obtained by using the product described in Preparation J in Stage F.

Elemental microanalysis:

|  | C % | H % | N % | S % |
|---|---|---|---|---|
| calculated | 57.45 | 6.38 | 7.88 | 4.51 |
| found | 57.57 | 6.75 | 7.91 | 4.32 |

EXAMPLE 25

4-(4-Chlorophenylureidosulfonyl)benzoyl-(S)-Val-(S)-Abo-(R,S)-Val-$CF_3$

The expected product is obtained by using the product described in Preparation K in Stage F.

Elemental microanalysis:

|  | C % | H % | N % | Cl % | S % |
|---|---|---|---|---|---|
| calculated | 53.40 | 5.30 | 9.44 | 4.78 | 4.32 |
| found | 53.86 | 5.28 | 9.55 | 4.22 | 4.77 |

EXAMPLE 26

4-(4-Chlorophenylureidosulfonyl)benzoyl-(S)-Val-(2S,3aS,7aS)-Phi-(R,S)-Val-$CF_3$ The expected product is obtained by using the product described in Preparation K in Stage F.

Elemental microanalysis:

|  | C % | H % | N % | Cl % | S % |
|---|---|---|---|---|---|
| calculated | 51.54 | 5.72 | 8.84 | 4.47 | 4.05 |
| found | 51.74 | 5.85 | 8.53 | 4.09 | 3.65 |

EXAMPLE 27

4-[(Dicyclopropylmethyl)carbonylaminosulfonyl]benzoyl-(S)-Val-(2S,3aS,7aS)-Phi-(R,S)-Val-$CF_3$ The expected product is obtained by using the product described in Preparation J in Stage F.

Elemental microanalysis:

|  | C % | H % | N % | S % |
|---|---|---|---|---|
| calculated | 58.00 | 6.54 | 7.73 | 4.42 |
| found | 58.20 | 6.91 | 7.95 | 4.38 |

EXAMPLE 28

4-[(Adamant-1-yl)carbonylaminosulfonyl]benzoyl-(S)-Val-(S)-Abo-(R,S)-Val-$CF_3$

The expected product is obtained by using the product described in Preparation L in Stage F.

Elemental microanalysis:

|  | C % | H % | N % | S % |
|---|---|---|---|---|
| calculated | 59.18 | 6.58 | 7.46 | 4.26 |
| found | 59.18 | 7.04 | 8.05 | 4.10 |

EXAMPLE 29

4-[(3,5-Di-tert-butyl-4-hydroxybenzyl)carbonylaminosulfonyl]benzoyl-(S)-Val-(2S,3aS,7aS)-Phi-(R,S)-Val-$CF_3$ The expected product is obtained by using the product described in Preparation M in Stage F.

Elemental microanalysis:

|  | C % | H % | N % | S % |
|---|---|---|---|---|
| calculated | 60.83 | 7.00 | 6.60 | 3.78 |
| found | 60.67 | 7.33 | 6.97 | 3.85 |

EXAMPLE 30

4-[4-(2,6-Dimethyl-3,5-diethoxycarbonyl-1,4-dihydropyrid-4-yl)benzoylaminosulfonyl]benzoyl-(S)-Val-(S)-Abo-(R,S)-Val-$CF_3$ The expected product is obtained by using the product described in Preparation N in Stage F.

Elemental microanalysis:

|  | C % | H % | N % | S % |
|---|---|---|---|---|
| calculated | 58.53 | 5.98 | 7.42 | 3.40 |
| found | 57.86 | 5.94 | 7.12 | 3.30 |

EXAMPLE 31

4-{4-[2-(3,5-Di-tert-butyl-4-hydroxyphenylthio)ethyl]benzoylaminosulfonyl}benzoyl-(S)-Val-(2S,3aS,7aS)-Phi-(R,S)-Val-$CF_3$ The expected product is obtained by using the product described in Preparation E in Stage F.

Elemental microanalysis:

|  | C % | H % | N % | S % |
|---|---|---|---|---|
| calculated | 61.84 | 6.75 | 5.77 | 6.60 |
| found | 61.73 | 7.04 | 5.49 | 5.49 |

EXAMPLE 32

4-{4-[2-(1-Oxa-2-oxo-3,8-diazaspiro[4.5]dec-8-yl)ethyl]benzoylaminosulfonyl}benzoyl-(S)-Val-(2S,3aS,7aS)-Phi-(R,S)-Val-$CF_3$ The expected product is obtained by using the product described in Preparation O in Stage F.

Mass spectrum: FAB–$[M]^+$: m/z=888 (theoretical mass: M=888 )

EXAMPLE 33

4-{[4-Chloro-3-[(3,5-di-tert-butyl-4-hydroxybenzyl)carbonylaminosulfonyl]benzoyl]aminosulfonyl}benzoyl-(S)-Val-(2S,3aS,7aS)-Phi-(R,S)-Val-CF$_3$ The expected product is obtained by using the product described in Preparation P in Stage F.

Elemental microanalysis:

|            | C %   | H %  | N %  | S %  |
|------------|-------|------|------|------|
| calculated | 56.30 | 5.95 | 6.57 | 6.01 |
| found      | 56.16 | 6.45 | 6.67 | 6.08 |

EXAMPLE 34

4-{[3,5-Di-tert-butyl-4-(3,5-di-tert-butyl-4-hydroxybenzoyloxy)benzoyl]aminosulfonyl}-benzoyl-(S)-Val-(2S,3aS,7aS)-Phi-(R,S)-Val-CF$_3$ The expected product is obtained by using the product described in Preparation Q in Stage F.

Elemental microanalysis:

|            | C %   | H %  | N %  | S %  |
|------------|-------|------|------|------|
| calculated | 64.14 | 7.27 | 5.25 | 3.00 |
| found      | 63.81 | 7.32 | 5.39 | 3.73 |

EXAMPLE 35

4-{[4-Methoxy-3-(3-ethoxy-2-hydroxypropoxy)-benzoyl]aminosulfonyl}benzoyl-(S)-Val-(2S,3aS,7aS)-Phi-(R,S)-Val-CF$_3$ The expected product is obtained by using the product described in Preparation R in Stage F.

Mass spectrum: FAB−[M−H]$^-$: m/z=853 (theoretical mass: M=854)

EXAMPLE 36

4-[(3,5-Di-tert-butyl-4-hydroxybenzoyl)aminosulfonyl]benzoyl-(S)-Val-(2S,3aS,7aS)Phi-(R,S)-Val-CF$_3$ The expected product is obtained by using the product described in Preparation S in Stage F.

Elemental microanalysis:

|            | C %   | H %  | N %  | S %  |
|------------|-------|------|------|------|
| calculated | 60.42 | 6.88 | 6.71 | 3.84 |
| found      | 60.84 | 7.28 | 6.92 | 4.21 |

EXAMPLE 37

4-{4-[3,5-Di-tert-butyl-4-(ethoxymethoxy)benzyloxy]benzoylaminosulfonyl}benzoyl-(S)-Val-(2S,3aS,7aS)-Phi-(R,S)-Val-CF$_3$ The expected product is obtained by using the product described in Preparation T in Stage F.

Elemental microanalysis:

|            | C %   | H %  | N %  | S %  |
|------------|-------|------|------|------|
| calculated | 62.51 | 6.96 | 5.61 | 3.21 |
| found      | 62.17 | 7.37 | 5.74 | 3.23 |

EXAMPLE 38

4-[(3,5-Di-tert-butyl-4-hydroxyphenylthio)acetylaminosulfonyl]benzoyl-(S)-Val-(2S,3aS,7aS)-Phi-(R,S)-Val-CF$_3$ The expected product is obtained by using the product described in Preparation U in Stage F.

Elemental microanalysis:

|            | C %   | H %  | N %  | S %  |
|------------|-------|------|------|------|
| calculated | 58.62 | 6.75 | 6.36 | 7.28 |
| found      | 58.79 | 7.12 | 6.02 | 7.93 |

EXAMPLE 39

4-{[3-(3,5-Di-tert-butyl-4-ethoxymethoxyphenyl)-trans-acryloyl]aminosulfonyl}benzoyl-(S)-Val-(2S,3aS,7aS)-Phi-(R,S)-Val-CF$_3$ The expected product is obtained by using the product described in Preparation V in Stage F.

Elemental microanalysis:

|            | C %   | H %  | N %  | S %  |
|------------|-------|------|------|------|
| calculated | 61.42 | 7.13 | 6.10 | 3.49 |
| found      | 61.22 | 7.10 | 6.10 | 3.43 |

EXAMPLE 40

4-{[3-(3,5-Di-tert-butyl-4-hydroxyphenyl)trans-acryloyl]aminosulfonyl}benzoyl-(S)-Val-(2S,3aS,7aS)-Phi-(R,S)-Val-CF$_3$ The expected product was obtained after hydrolysis in dioxane/hydrochloric acid medium of the compound described in Example 39 and purification by chromatography on a silica column, using a dichloromethane/methanol (95/5) mixture as eluent.

Elemental microanalysis:

|            | C %   | H %  | N %  | S %  |
|------------|-------|------|------|------|
| calculated | 61.38 | 7.22 | 6.42 | 4.18 |
| found      | 61.12 | 6.91 | 6.51 | 3.72 |

EXAMPLE 41

4-(4-Chlorophenylsulfonylaminocarbonyl)benzoyl-
[N-(3,5-di-tert-butyl-4-hydroxyphenyl)acetyl]-(S)-
Lys-(2S,3aS,7aS)-Phi-(R,S)-Val-CF$_3$ Stage A: 4-(4-Chlorophenylsulfonylaminocarbonyl)benzoyl-(S)-Lys-OCH$_3$ 4-(4-Chlorophenylsulfonylaminocarbonyl)benzoic acid is coupled with the methyl ester of (S)-lysine, protected by a tert-butoxy group on its side amine functional group, by using BOP as a coupling reagent in the presence of diethylamine in dimethylformamide. The expected product is then deprotected by acid hydrolysis with the aid of hydrobromic acid in acetic acid medium and is purified by chromatography on a silica column, using a dichloromethane/methanol (60/40) mixture as eluent.

Stage B: 4-(4-Chlorophenylsulfonylaminocarbonyl)benzoyl-[N-(3,5-di-tert-butyl-4-hydroxyphenyl)acetyl]-(S)-Lys-OH The compound obtained in the preceding stage is coupled, according to the technique of W. Konig and R. Geiger (Chem. Ber., 103, 788, 1970) with 3,5-di-tert-butyl-4-hydroxyphenylacetic acid. The expected product, in the form of a methyl ester, is purified by chromatography on a silica column, using a dichloromethane/methanol (90/10) mixture as eluent, and is then saponified with a sodium hydroxide/ethanol mixture.

Stage C: 4-(4-Chlorophenylsulfonylaminocarbonyl)benzoyl-[N-(3,5-di-tert-butyl-4-hydroxyphenyl)acetyl]-(S)-Lys-( 2S, 3aS, 7 aS)-Phi-(R,S)-Val-CF$_3$ The product obtained in the preceding stage is coupled with (S)-Phi-(R,S)-Val-CF$_3$, according to the technique described in the preceding stage, and taken to the expected product which is purified by chromatography on a silica column, using a dichloromethane/methanol (90/10 ) mixture as eluent.

Elemental microanalysis:

|  | C % | H % | N % | S % |
|---|---|---|---|---|
| calculated | 60.26 | 6.44 | 6.89 | 3.15 |
| found | 59.37 | 6.59 | 6.43 | 2.77 |

Examples 42 and 43 were obtained according to the process described for Example 41.

EXAMPLE 42

4-(4-Chlorophenylsulfonylaminocarbonyl)benzoyl-[N-(3,5-di-tert-butyl-4-hydroxyphenylthio)butyroyl]-(S)-Lys-(2S,3aS,7aS)-Phi-(R,S)-Val-CF$_3$ Mass spectrum: FAB: [M+H]$^+$: m/z=1076 (theoretical mass: M=1075)

EXAMPLE 43

4-(4-Chlorophenylsulfonylaminocarbonyl)benzoyl-[S-(3,5-di-tert-butyl-4-hydroxy-phenyl)]-(S)-Cys-(2S,3aS,7aS)-Phi-(R,S)-Val-CF$_3$ Mass spectrum: FAB: [M+H]$^+$: m/z=949 (theoretical mass: M=948)

EXAMPLE 44

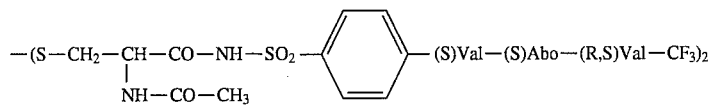

The expected product was obtained by hydrolysis of the compound of Example 18 in a dioxane/water (80/20) mixture in the presence of hydrogen sulfide and of mercuric acetate.

After filtration, the filtrate is evaporated and taken to the expected product.

Elemental microanalysis:

|  | C % | H % | N % | S % |
|---|---|---|---|---|
| calculated | 50.81 | 5.64 | 9.56 | 8.75 |
| found | 51.42 | 5.58 | 9.50 | 8.32 |

PHARMACOLOGICAL STUDY OF THE DERIVATIVES OF THE INVENTION

EXAMPLE 45

Inhibitory activity for human leucocyte elastase in vitro

The strength of the compounds of the invention is determined by the level of inhibition of the action of human leucocyte elastase on a low molecular weight peptide substrate according to the technique described by B. M. Ashe et al., (J. Biol. Chem., 256, 11603–11606, 1981). This activity is measured by following the kinetics of hydrolysis of the substrate which leads to the release of paranitroaniline which absorbs at a wavelength of 410 nm.

Reagent:
  Enzyme: Human sputum leucocyte elastase (Elastin Products Co.) solubilized at 1000 ul/ml of distilled water, and frozen in aliquots of 50 µl at −20° C.
  Substrate: methoxysuccinyl-L-alanyl-L-alanyl-propyl-valine paranitroanilide (Sigma chimie).
  Buffer: Tris 0.1M; NaCl 0.5M; pH=7.8.

Equipment:
  Spectrophotometer thermostatically controlled at 37° C., equipped with a cell changer.
  1 ml polystyrene cell.
  Dry waterbath adjusted to 37° C.

Procedure:
  The following are introduced into a cell:

970 μl of buffer

10 μl of the product to be tested or of the solvent (concentrated×100)

10 μl of human sputum leucocyte elastase diluted to 1/10th

Stirring and incubation for 15 min at 37° C.

The reaction is started by addition of 10 μl of substrate.

The cell is introduced into the spectro- photometer, and the optical density is recorded as a function of time at 410 nm at 37° C.

The initial rate is measured for each product concentration (or solvent control) studied.

Percentages of inhibition with respect to the solvent control are calculated:

Percentage of inhibition=100×(control rate−rate of the product tested/control rate).

The inhibitory concentrations 50 ($IC_{50}$) are calculated from the percentages of inhibition by simple linear regression.

The results obtained in this test are collated below:

| Example | $IC_{50}$ (nM) | Example | $IC_{50}$ (nM) |
|---|---|---|---|
| 1 | 24 | 28 | 47 |
| 2 | 25 | 29 | 38 |
| 4 | 15 | 30 | 41 |
| 6 | 27 | 31 | 40 |
| 14 | 30 | 32 | 42 |
| 18 | 19 | 33 | 34 |
| 22 | 19 | 35 | 37 |
| 23 | 30 | 36 | 36 |
| 24 | 25 | 40 | 38 |
| 25 | 34 | 41 | 70 |
| 26 | 31 | 44 | 14 |
| 27 | 29 | | |

EXAMPLE 46

In vivo inhibitory activity: model of acute hemorrhagic edema in hamsters

Tracheal instillation in hamsters of a purified preparation of human sputum leucocyte elastase leads to acute hemorrhaging which can be quantified by measuring the concentration of hemoglobin in the broncho-alveolar washing 3 hours after the elastase instillation.

The study is carried out on male hamsters weighing 120 to 100 g (Syrian Golden, n=10 per batch). The animals are anesthetized with pentobarbital at a dose of 40 mg/kg intraperitoneally.

The hamsters are anesthetized and the trachea is exposed surgically. The products to be tested are administered with the aid of a needle directly into the trachea in a volume of 0.1 ml at a dose of 10 μg. Human sputum leucocyte elastase is administered, 3 hours after administration of the product, intratracheally at a dose of 50 units per animal at a volume of 0.2 ml.

The animals are sacrificed with the aid of a lethal dose of pentobarbital 3 hours after instillation of elastase and a broncho-alveolar washing with physiological serum is carried out. The degree of hemorrhaging is quantified by a colorimetric method which makes it possible to quantitatively determine the hemoglobin concentration (Boehringer hemoglobin test combination).

The results are expressed in percentage of inhibition of hemorrhaging.

The compounds of the present invention are effective inhibitors of human leucocyte elastase which prevent or reduce the hemorrhaging induced by intratracheal instillation of human leucocyte elastase. The results obtained in this test are collated below:

| Example | Inhibition (%) | Example | Inhibition (%) |
|---|---|---|---|
| 1 | 67 | 27 | 38 |
| 2 | 57 | 28 | 57 |
| 4 | 70 | 29 | 63 |
| 6 | 77 | 30 | 56 |
| 14 | 28 | 31 | 20 |
| 18 | 38 | 32 | 42 |
| 22 | 65 | 33 | 37 |
| 23 | 61 | 35 | 47 |
| 24 | 46 | 36 | 53 |
| 25 | 63 | 40 | 40 |
| 26 | 64 | 41 | 41 |
| | | 44 | 44 |

EXAMPLE 47

Study of lipid peroxidation

The study was carried out on rat hepatic microsomes in the presence of $Fe^{3+}$ (100 μM) and of ascorbate (100 μM). Quantitative determination of malondialdehyde (MDA) is carried out by the thiobarbituric acid method (spectrophotometry λ=532 nm) according to the technique described by N. Paya et al. (Biochem. Pharmacol., Vol. 44, No. 2, p. 205–214, 1992).

The products of the invention have an inhibitory activity of between $10^{-6}$M and $10^{-5}$M on lipid peroxidation in the system studied.

EXAMPLE 48

Pharmaceutical composition

Preparation formula for 1000 tablets each containing 10 mg of active material
Compound of Example 6 . . . 10 g
Hydroxypropyl cellulose . . . 2 g
Wheat starch . . . 10 g
Lactose . . . 100 g
Magnesium stearate . . . 3 g
Talc . . . 3 g

We claim:

1. A compound of formula (I):

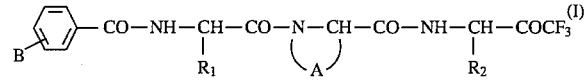

wherein:

$R_1$ represents linear or branched ($C_1$–$C_6$)alkyl which is unsubstituted or substituted by amino, (3,5-di-tert-butyl- 4-hydroxy)benzylcarbonylamino, (3,5-di-tert-butyl-4-hydroxy)phenylthio or 3-[(3,5-di-tert-butyl-4-hydroxy)phenylthio]propylcarbonylamino, $R_2$ represents linear or branched ($C_1$–$C_6$)alkyl, A represents, with the nitrogen and carbon atoms to which it is attached, a 2-azabicyclo[2.2.2]octane, 2-azabicyclo[2.2.1]heptane, perhydroindole, perhydroisoindole, indoline, isoindoline, perhydroquinoline, perhydroisoquinoline, 1,2,3,4-tetra-hydroquinoline, cyclopenta[b] pyrrolidine or 1,3-thiazolidine ring, B represents any one of the following radicals:

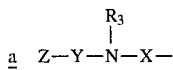
a   Z—Y—N—X— wherein:

R$_3$ represents hydrogen or linear or branched (C$_1$–C$_6$)alkyl which is unsubstituted or substituted by phenyl, X, Y, which are different, represent CO or SO$_2$, Z represents linear or branched (C$_1$–C$_6$)alkyl which is substituted by one or two, identical or different, (C$_3$–C$_7$)cycloalkyl or (C$_1$–C$_4$)trihaloalkyl, adamant-1-yl, phenyl which is unsubstituted or substituted by one or a number of, identical or different, halogen or linear or branched (C$_1$–C$_6$)alkyl, hydroxyl, linear or branched (C$_1$–C$_6$)alkoxy, (C$_1$C$_4$)trihaloalkyl, cyano, 1,4-dihydropyrid-4-yl (unsubstituted or substituted by one or a number of, identical or different, linear or branched (C$_1$–C$_6$)alkyl or linear or branched (C$_1$–C$_6$)-alkoxycarbonyl radicals), (3,5-di-tert-butyl-4-hydroxy)benzylcarbonylaminosulfonyl, (3,5-di-tert-butyl- 4-hydroxy)benzoyloxy, (3-ethoxy-2-hydroxy)propoxy or [3,5-di-tert-butyl-4-(ethoxymethoxy)]benzyloxy, or, (C$_1$–C$_4$)alkenyl substituted by [3,5-di-tert-butyl-4-(ethoxy-methoxy)]phenyl or (3,5-di-tert-butyl-4-hydroxy)phenyl,

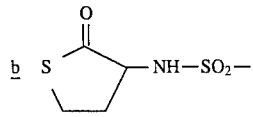
b

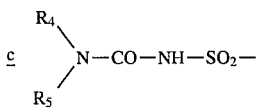
c wherein:

R$_4$ and R$_5$, which are identical or different, represent: hydrogen or linear or branched (C$_1$–C$_6$)alkyl (unsubstituted or substituted by phenyl), phenyl (unsubstituted or substituted by one or a number of halogen or linear or branched (C$_1$–C$_6$)alkyl, linear or branched (C$_1$–C$_6$)alkoxy or (C$_1$–C$_4$)trihaloalkyl radicals), 3-azabicyclo[3.3.0]oct-3-yl, 4-(2,3,4-trimethoxybenzyl)piperazino, morpholino, pyrrolidino, piperidino, azetidino or 1-oxa-3,8-diaza-2-oxospiro[4.5]dec-8-yl (unsubstituted or substituted by linear or branched (C$_1$–C$_6$)alkyl or linear or branched (C$_1$–C$_6$)phenylalkyl), or form, with the nitrogen atom to which they are attached, any one of the following rings:
3-azabicyclo[3.3.0]octane,
4-(2,3,4-trimethoxybenzyl)piperazine,
morpholine,
pyrrolidine,
azetidine,
3,8-diaza-1-oxa-2-oxospiro[4.5]decane which is unsubstituted or substituted by a linear or branched (C$_1$–C$_6$)alkyl or linear or branched (C$_1$–C$_6$)phenylalkyl radical,

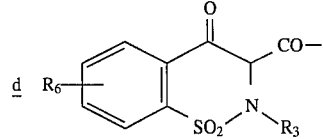
d wherein:

R$_3$ is as defined above and

R$_6$ represents hydrogen or halogen or linear or branched (C$_1$–C$_6$)alkyl, linear or branched (C$_1$–C$_6$)alkoxy, (C$_1$–C$_4$)trihaloalkyl or cyano,

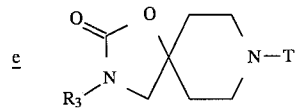
e wherein:

R$_3$ is as defined above,

T represents any one of the following groups:
—(CH$_2$)$_m$—,
—SO$_2$—NH—CO—,
—CO—NH—SO$_2$—,

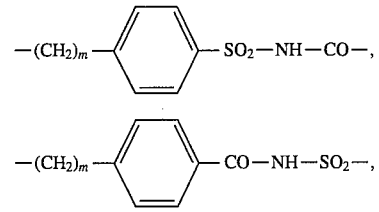

such that m is an integer between 1 and 4, inclusive

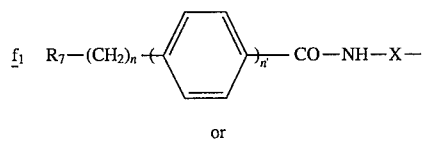
f$_1$   R$_7$—(CH$_2$)$_n$—⟨phenyl⟩$_{n'}$—CO—NH—X— or f$_2$   R$_7$—(CH$_2$)$_n$— wherein:

X is as defined above, n is equal to 0, 1, 2 or 3, n' is equal to 0 or 1,

R$_7$ represents:
3,5-di-tert-butyl-4-hydroxyphenyl,
3,5-di-tert-butyl-4-hydroxyphenoxy,
or 3,5-di-tert-butyl-4-hydroxyphenylthio,

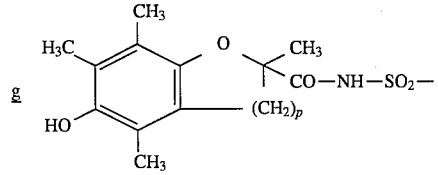
g wherein p is equal to 1 or 2, h 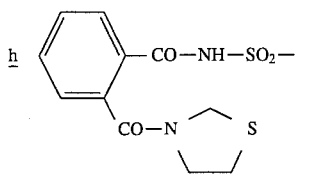

i 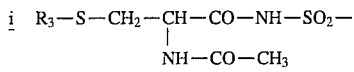

wherein $R_3$ is as defined above, j 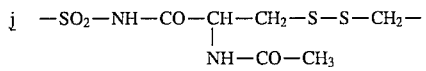

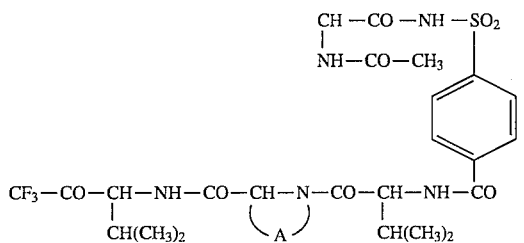

wherein A is as defined above, which compound of formula (I) comprises the corresponding hydrates of the $COCF_3$ ketone functional group, its enantiomers, diastereoisomers and epimers, and its addition salts with a pharmaceutically acceptable acid or base.

2. The compound of formula (I) as claimed in claim 1, wherein B represents

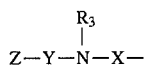

wherein:

$R_3$ represents hydrogen or linear or branched $(C_1-C_6)$alkyl which is unsubstituted or substituted by phenyl, X, Y, which are different, represent CO or $SO_2$, Z represents linear or branched $(C_1-C_6)$alkyl which is substituted by one or two, identical or different, $(C_3-C_7)$cycloalkyl or $(C_1-C_4)$trihaloalkyl, adamant-1-yl, phenyl which is unsubstituted or substituted by one or a number of, identical or different, halogen or linear or branched $(C_1-C_6)$alkyl, hydroxyl, linear or branched $(C_1-C_6)$alkoxy, $(C_1-C_4)$trihaloalkyl, cyano, 1,4-dihydropyrid-4-yl (unsubstituted or substituted by one or a number of, identical or different, linear or branched $(C_1-C_6)$alkyl or linear or branched $(C_1-C_6)$alkoxycarbonyl), (3,5-di-tert-butyl-4-hydroxy)benzylcarbonyl-aminosulfonyl, (3,5-di-tert-butyl- 4-hydroxy)benzoyloxy, (3-ethoxy-2-hydroxy)propoxy or [3,5-di-tert-butyl-4-(ethoxymethoxy)]benzyloxy, or, $(C_1-C_4)$alkenyl substituted by [3,5-di-tert-butyl-4-(ethoxymethoxy)]phenyl or (3,5-di-tert-butyl-4-hydroxy)phenyl, its hydrates, enantiomers, diastereoisomers and epimers, and its addition salts with a pharmaceutically acceptable acid or base.

3. The compound of formula (I) as claimed in claim 1, wherein B represents

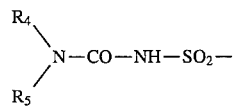

wherein:

$R_4$ and $R_5$, which are identical or different, represent:
hydrogen or linear or branched $(C_1-C_6)$alkyl, phenyl (unsubstituted or substituted by one or a number of halogen or linear or branched $(C_1-C_6)$alkyl, linear or branched $(C_1-C_6)$alkoxy or $(C_1-C_4)$trihaloalkyl), 3-azabicyclo[3.3.0]oct-3-yl, 4-(2,3,4-trimethoxybenzyl)piperazino, morpholino, pyrrolidino, piperidino, azetidino or 1-oxa-3,8-diaza-2-oxospiro[4,5]dec-8-yl (unsubstituted or substituted by linear or branched $(C_1-C_6)$alkyl or linear or branched $(C_1-C_6)$phenylalkyl radical), or form, with the nitrogen atom to which they are attached, any one of the following rings:
3-azabicyclo[3.3.0]octane,
4-(2,3,4-trimethoxybenzyl)piperazine,
morpholine,
pyrrolidine,
azetidine,
3,8-diaza-1-oxa-2-oxospiro[4.5]decane which is unsubstituted or substituted by a linear or ranched $(C_1-C_6)$alkyl or linear or branched $(C_1-C_6)$phenylalkyl, its hydrates, enantiomers, diastereoisomers and epimers, and its addition salts with a pharmaceutically acceptable acid or base.

4. The compound of formula (I) as claimed in claim 1, wherein B represents

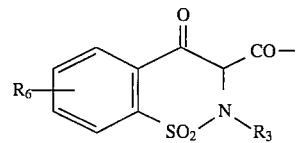

wherein:

$R_3$ is as defined above and $R_6$ represents hydrogen or halogen or linear or branched $(C_1-C_6)$alkyl, linear or branched $(C_1-C_6)$alkoxy, $(C_1-C_4)$trihaloalkyl or cyano, its hydrates, enantiomers, diastereoisomers and epimers, and its addition salts with a pharmaceutically acceptable acid or base.

5. The compound of formula (I) as claimed in claim 1, wherein B represents:

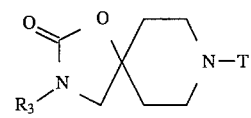

in which:

$R_3$ is as defined above,

T represents any one of the following groups:
—$(CH_2)m$—,
—$SO_2$—NH—CO—,

—CO—NH—SO$_2$—,

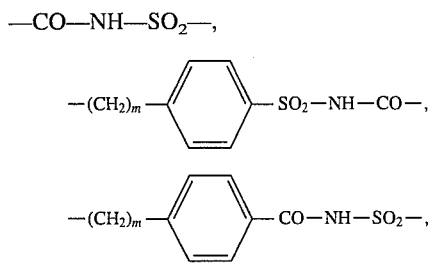

such that m is an integer between 1 and 4, inclusive its hydrates, enantiomers, diastereoisomers and epimers, and its addition salts with a pharmaceutically acceptable acid or base.

6. The compound of formula (I) as claimed in claim 1, wherein B represents:

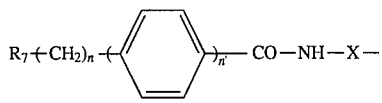

in which:
X is as defined above,
n is equal to 0, 1, 2 or 3,
n' is equal to 0 or 1,
R$_7$ represents:
  3,5-di-tert-butyl-4-hydroxyphenyl,
  3,5-di-tert-butyl-4-hydroxyphenoxy,
  or 3,5-ditert-butyl-4-hydroxyphenylthio
its hydrates, enantiomers, diastereoisomers and epimers, and its addition salts with a pharmaceutically acceptable acid or base.

7. The compound of formula (I) as claimed in claim 1, wherein A represents, with the nitrogen and carbon atoms to which it is attached, a 2-azabicyclo[2.2.2]octane ring, its hydrates, enantiomers, diastereoisomers and epimers, and its addition salts with a pharmaceutically acceptable acid or base.

8. The compound of formula (I) as claimed in claim 1, wherein A represents, with the nitrogen and carbon atoms to which it is attached, a perhydroindole ring, its hydrates, enantiomers, diastereoisomers and epimers, and its addition salts with a pharmaceutically acceptable acid or base.

9. The compound of formula (I) as claimed in either of claims 7 or 8, wherein B represents 4-chlorobenzoyl-aminosulfonyl, its hydrates, enantiomers, diastereoisomers and epimers, and its addition salts with a pharmaceutically acceptable acid or base.

10. The compound of formula (I) as claimed in either of claims 7 or 8, wherein B represents 4-chlorophenylsulfonylaminocarbonyl, its hydrates, enantiomers, diastereoisomers and epimers, and its additional salts with a pharmaceutically acceptable acid or base.

11. The compound of formula (I) as claimed in claim 1, which is 4-(4-chlorophenylsulfonylaminocarbonyl)-benzoyl-(S)-Val-(2 S,3aS,7aS)-Phi-(R,S)-Val-CF$_3$, Phi representing a perhydroindole-2-carbonyl residue and Val a valyl residue, its hydrates and isomers, and its addition salts with a pharmaceutically acceptable acid or base.

12. The compound of formula (I) as claimed in claim 1, which is 4-(4-chlorophenylsulfonylaminocarbonyl)-benzoyl-(S)-Val-(S)-Abo-(R,S)-Val-CF$_3$, Abo representing a 2-azabicyclo[2.2.2]octane-3-carbonyl residue and Val a valyl residue, its hydrates and isomers, and its addition salts with a pharmaceutically acceptable acid or base.

13. A method for treating a living animal body afflicted with emphysema comprising the step of administering to the living body an amount of a compound of claim 1 which is effective for alleviation of said condition.

14. A pharmaceutical composition useful in the treatment of emphysema comprising as active principle an effective amount of a compound as claimed in claim 1, together with one or more pharmaceutically acceptable excipients or vehicles.

15. A compound of claim 1 which is selected from 4-[(3,5-di-tert-butyl- 4-hydroxybenzyl)carbonylaminosulfonyl]benzoyl-(S)-Val-(2 S,3aS,7aS)-Phi(R,S)-Val-CF$_3$, Phi representing a perhydroindole- 2-carbonyl residue and Val a valyl residue, its hydrates and isomers, and its addition salts with a pharmaceutically-acceptable acid or base.

16. A compound of claim 1 which is selected from 4-{[4-chloro-3-[(3,5-di-tert-butyl-4-hydroxybenzyl)carbonylaminosulfonyl]benzoyl]aminosulfonyl}benzoyl-(S)-Val-(2S,3aS,7aS)-Phi-(R,S)-Val-CF$_3$, Phi representing a perhydroindole-2-carbonyl residue and Val a valyl residue, its hydrates and isomers, and its addition salts with a pharmaceutically-acceptable acid or base.

17. A compound of claim 1 which is selected from 4-{[4-methoxy- 3-(3-ethoxy-2-hydroxypropoxy)benzoyl]aminosulfonyl}benzoyl-(S)-Val-(2 S,3aS,7aS)-Phi-(R,S)-Val-CF$_3$, Phi representing a perhydro-indole- 2-carbonyl residue and Val a valyl residue, its hydrates and isomers, and its addition salts with a pharmaceuticallyacceptable acid or base.

18. A compound of claim 1 which is selected from 4-[(3,5-di-tert-butyl- 4-hydroxyphenylthio)acetylaminosulfonyl]benzoyl-(S)-Val-(2 S,3aS,7aS)-Phi-(R,S)-Val-CF$_3$, Phi representing a perhydro-indole- 2-carbonyl residue and Val a valyl residue, its hydrates and isomers, and its addition salts with a pharmaceutically-acceptable acid or base.

19. A compound of claim 1 which is selected from 4-[(3,5-di-tert-butyl-4 -hydroxybenzoyl)aminosulfonyl]benzoyl-(S)-Val-(2 S,3aS,7aS)-Phi-(R,S)-Val-CF$_3$, Phi representing a perhydro-indole- 2-carbonyl residue and Val a valyl residue, its hydrates and isomers, and its addition salts with a pharmaceutically-acceptable acid or base.

* * * * *

UNITED STATES PATENT AND TRADEMARK OFFICE
CERTIFICATE OF CORRECTION

PATENT NO. : 5,565,429
DATED : Oct. 15, 1996
INVENTOR(S) : M. Vincent; G. de Nanteuil; G. Remond; B. Portevin; Y. Herve; E. Canet; M. Lonchampt Page 1 of 4

It is certified that error appears in the above-indentified patent and that said Letters Patent is hereby corrected as shown below:

Column 2, line 7: Insert "B" at beginning of line before "represents".

Column 2, line 57: "[3.3.01" should read -- [3.3.0].

Column 4, line 55: "a" at beginning of line should read -- $\underline{a}$ --.

Column 5, line 66: "b" at beginning of line should read -- $\underline{b}$ --.

Column 10, line 21: "nopropyl)-3ethylcarbodiimide" should read -- nopropyl)-3-ethylcarbodiimide --.

Column 10, line 37: Insert a -- - -- (dash) at the end of the line.

Column 10, line 38: Delete the "-" at the beginning of the line.

Column 10, line 60: Delete the "-" at the end of the line and insert -- ) --.

Column 10, line 61: Delete the ")" at the beginning of the line.

Column 10, line 64: Delete the "-" at the end of the line and insert -- ) --.

UNITED STATES PATENT AND TRADEMARK OFFICE
CERTIFICATE OF CORRECTION

PATENT NO. : 5,565,429
DATED : Oct. 15, 1996
INVENTOR(S) : M.Vincent; G. de Nanteuil; G. Remond; B. Portevin; Y. Herve; E. Canet; M. Lonchampt It is certified that error appears in the above-indentified patent and that said Letters Patent is hereby corrected as shown below:

Column 10, line 65: Delete the ")" at the beginning of the line.

Column 12, line 46: "pfonyl}" should read -- fonyl} --.

Column 13, line 40: "for Examples and 5." should read -- for Examples 4 and 5. --.

Column 14, line 3: "Example is a" should read -- Example 9 is a --.

Column 15, line 44: Insert -- $_3$ -- at end of the line, after "CF".

Column 15, line 45: Delete the "$_3$".

Column 16, line 60: Insert -- $_3$ -- at end of the line after "CF".

Column 15, line 61: Delete the "$_3$".

Column 16, line 14: "-1-so-" at end of the line should read -- -1-iso- --.

Column 16, line 33: Delete excessive space in the line.

Column 17, line 24: Delete the "(" at the end of the line.

Column 17, line 25: Insert -- ( -- at the beginning of the line.

UNITED STATES PATENT AND TRADEMARK OFFICE
CERTIFICATE OF CORRECTION

PATENT NO. : 5,565,429
DATED : Oct. 15, 1996
INVENTOR(S) : M. Vincent; G. de Nanteuil; G. Remond; B. Portevin; Y. Herve; E. Canet; M. Lonchampt Page 3 of 4

It is certified that error appears in the above-indentified patent and that said Letters Patent is hereby corrected as shown below:

Column 18, line 43: Delete the "(" at the end of the line.

Column 18, line 44: Insert -- ( -- at the beginning of the line.

Column 20, line 37: Delete the "(" from the end of the line.

Column 20, line 38: Insert "(" at the beginning of the line.

Column 21, line 7: Delete excessive space in the line.

Column 21, line 25: Delete excessive space in the line.

Column 21, line 26: Delete the "-" from the end of the line and insert -- 1) --.

Column 21, line 27: Delete "1)" from the beginning of the line.

Column 21, line 76: Delete the "-" from the end of the line and insert -- 1) --.

Column 21, line 37: Delete "1)" from the beginning of the line.

Column 21, line 36: Delete excessive space in the line.

Column 21, line 53: "hydroxy-phenyl)]-" should read -- hydroxyphenyl)]- --.

UNITED STATES PATENT AND TRADEMARK OFFICE
CERTIFICATE OF CORRECTION

PATENT NO. : 5,565,429
DATED : Oct. 15, 1996
INVENTOR(S) : M. Vincent; G. de Nanteuil; G. Remond; B. Portevin; Y. Herve; E. Canet; M. Lonchampt It is certified that error appears in the above-indentified patent and that said Letters Patent is hereby corrected as shown below:

Column 23, lines 15 & 16: Lines should be in regular-size type.

Column 29, line 12: Insert a -- , -- (comma) after "inclusive".

Column 30, line 40: Insert a -- - -- (dash) between "pharmaceutically" and "acceptable".

Signed and Sealed this

Seventh Day of January, 1997

BRUCE LEHMAN

Attesting Officer     Commissioner of Patents and Trademarks